US012599782B2

(12) United States Patent
Teng et al.

(10) Patent No.: US 12,599,782 B2
(45) Date of Patent: *Apr. 14, 2026

(54) BORON NEUTRON CAPTURE THERAPY SYSTEM AND TREATMENT PLAN GENERATION METHOD THEREFOR

(71) Applicant: NEUBORON THERAPY SYSTEM LTD., Xiamen (CN)

(72) Inventors: Yi-chiao Teng, Xiamen (CN); Jiang Chen, Xiamen (CN)

(73) Assignee: NEUBORON THERAPY SYSTEM LTD., Xiamen (CN)

(*) Notice: Subject to any disclaimer, the term of this patent is extended or adjusted under 35 U.S.C. 154(b) by 360 days.

This patent is subject to a terminal disclaimer.

(21) Appl. No.: 18/131,416

(22) Filed: Apr. 6, 2023

(65) Prior Publication Data

US 2023/0241414 A1     Aug. 3, 2023

Related U.S. Application Data

(63) Continuation of application No. PCT/CN2021/119903, filed on Sep. 23, 2021.

(30) Foreign Application Priority Data

Oct. 14, 2020     (CN) .......................... 202011094034.3

(51) Int. Cl.
*A61N 5/10* (2006.01)
*G16H 20/40* (2018.01)
(Continued)

(52) U.S. Cl.
CPC ........... *A61N 5/1039* (2013.01); *G16H 20/40* (2018.01); *G16H 30/40* (2018.01); *G16H 50/50* (2018.01);
(Continued)

(58) Field of Classification Search
CPC .......... A61N 5/1039; A61N 2005/1034; A61N 2005/109; A61N 2005/1098; G16H 20/40; G16H 50/50; G16H 30/40
See application file for complete search history.

(56) References Cited

U.S. PATENT DOCUMENTS 12,172,031 B2 *  12/2024  Chen .................... A61N 5/1039
12,296,192 B2 *   5/2025  Chen .................... A61N 5/1071
(Continued)

FOREIGN PATENT DOCUMENTS

CN     106474634 A     3/2017
CN     106853272 A     6/2017
(Continued)

OTHER PUBLICATIONS

International Search Report of PCT/CN2021/119903, Dec. 14, 2021.

*Primary Examiner* — Nicole M Ippolito
(74) *Attorney, Agent, or Firm* — Troutman Pepper Locke LLP; Tim Tingkang Xia, Esq.

(57) ABSTRACT

A boron neutron capture therapy (BNCT) system includes a neutron beam irradiation device, a treatment planning module, and a control module. The neutron beam irradiation device is used to generate a therapeutic neutron beam during irradiation therapy and irradiate same to an irradiated body that has ingested a boron ($^{10}$B)-containing drug so as to form an irradiated site. According to medical image data of the irradiated site and a parameter of the therapeutic neutron beam generated by the neutron beam irradiation device, the treatment planning module performs a dosage simulation calculation and generates a treatment plan, the medical image data of the irradiated site comprising tissue-related information and boron ($^{10}$B) concentration-related information. The control module retrieves, from the treatment planning module, a treatment plan corresponding to the irradi- (Continued)

100 ated body, and controls the neutron beam irradiation device to perform irradiation therapy on the irradiated body according to the treatment plan.

20 Claims, 4 Drawing Sheets

(51) Int. Cl.
    *G16H 30/40*       (2018.01)
    *G16H 50/50*       (2018.01)

(52) U.S. Cl.
    CPC ............................ *A61N 2005/1034* (2013.01);
        *A61N 2005/109* (2013.01); *A61N 2005/1098*
                              (2013.01)

(56) References Cited

U.S. PATENT DOCUMENTS

| | | |
|---|---|---|
| 2016/0158578 A1 | 6/2016 | Liu et al. |
| 2018/0247452 A1 | 8/2018 | Liu et al. |
| 2018/0277278 A1 | 9/2018 | Liu et al. |
| 2018/0326225 A1 | 11/2018 | Liu et al. |
| 2019/0329067 A1 | 10/2019 | Liu et al. |

FOREIGN PATENT DOCUMENTS

| | | | |
|---|---|---|---|
| CN | 107427692 | A | 12/2017 |
| CN | 108310683 | A | 7/2018 |
| CN | 109308733 | A | 2/2019 |
| CN | 110013613 | A | 7/2019 |
| CN | 209253963 | U | 8/2019 |
| CN | 111629783 | A | 9/2020 |
| CN | 111803803 | A | 10/2020 |
| EP | 1658878 | A1 | 5/2006 |
| EP | 3357537 | A1 | 8/2018 |
| EP | 4166193 | A1 | 4/2023 |
| EP | 4197592 | A1 | 6/2023 |
| JP | 2012088771 | A | 5/2012 |
| JP | 2017035399 | A | 2/2017 |
| JP | 2018138194 | A | 9/2018 |
| JP | 2019501737 | A | 1/2019 |
| JP | 2019502505 | A | 1/2019 |
| JP | 2019130077 | A | 8/2019 |
| JP | 2020503959 | A | 2/2020 |
| JP | 2020111085 | A | 7/2020 |
| TW | 201719580 | A | 6/2017 |
| TW | I610086 | B | 1/2018 |
| TW | I666037 | B | 7/2019 |
| WO | 2017084459 | A1 | 5/2017 |

* cited by examiner

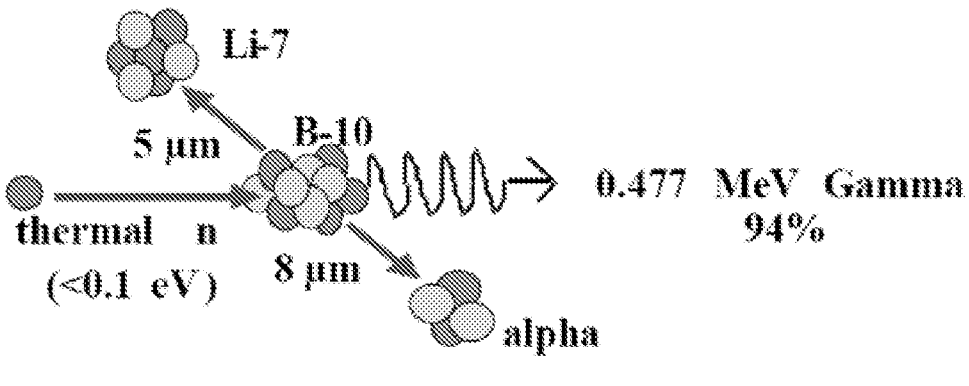
FIG. 1
$$^1n + {}^{10}B \longrightarrow {}^{11}B^* $$
$$^7Li + {}^4He + 2.79\ MeV \qquad (6.1\ \%)$$
$$^7Li^* + {}^4He + 2.31\ MeV \qquad (93.9\ \%)$$
$$\downarrow$$
$$^7Li + \gamma\text{-ray}\ (0.48\ MeV)$$
FIG. 2
<u>100</u>
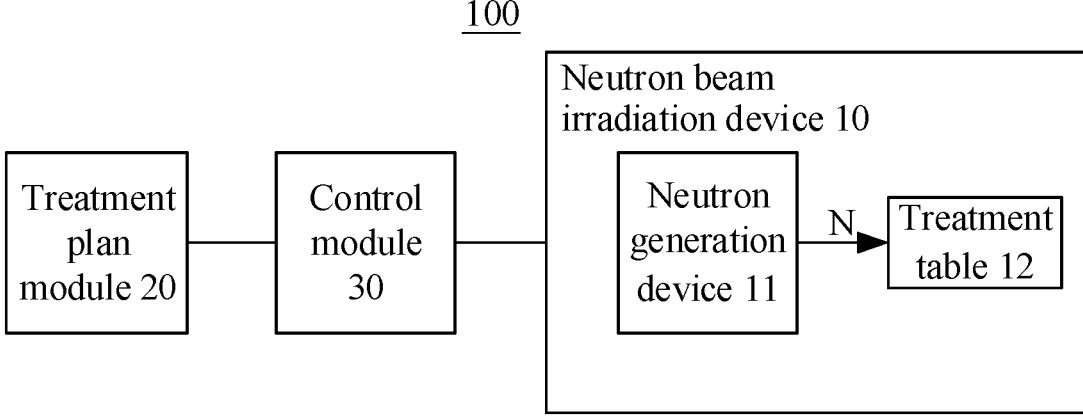
FIG. 3

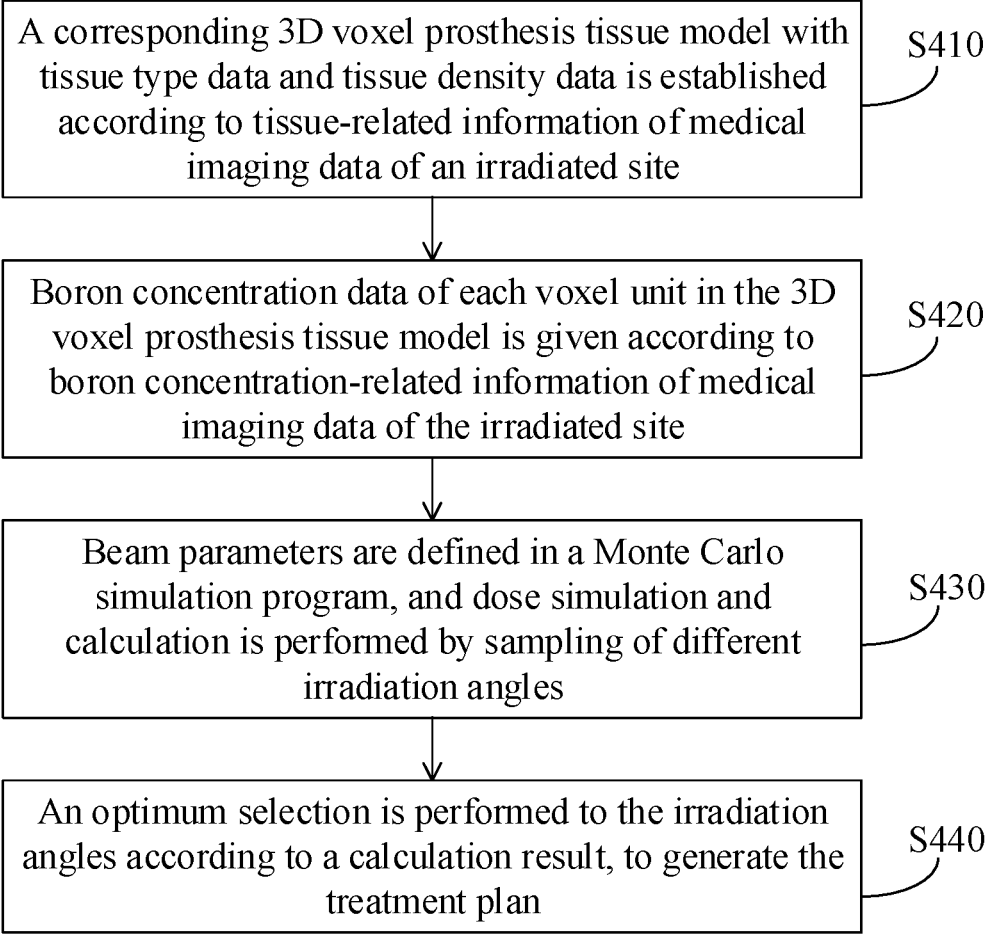

A corresponding 3D voxel prosthesis tissue model with tissue type data and tissue density data is established according to tissue-related information of medical imaging data of an irradiated site     S410

Boron concentration data of each voxel unit in the 3D voxel prosthesis tissue model is given according to boron concentration-related information of medical imaging data of the irradiated site     S420

Beam parameters are defined in a Monte Carlo simulation program, and dose simulation and calculation is performed by sampling of different irradiation angles     S430

An optimum selection is performed to the irradiation angles according to a calculation result, to generate the treatment plan     S440

FIG. 4

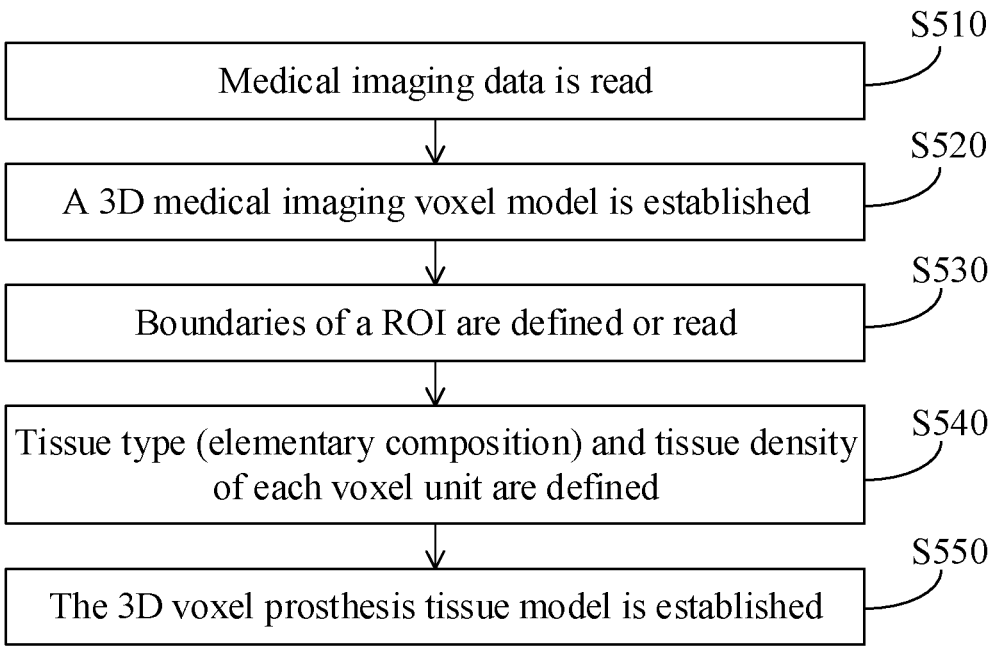

| | S510 |
| --- | --- |
| Medical imaging data is read | |

| | S520 |
| --- | --- |
| A 3D medical imaging voxel model is established | |

| | S530 |
| --- | --- |
| Boundaries of a ROI are defined or read | |

| | S540 |
| --- | --- |
| Tissue type (elementary composition) and tissue density of each voxel unit are defined | |

| | S550 |
| --- | --- |
| The 3D voxel prosthesis tissue model is established | |

FIG. 5

| | S610 |
| --- | --- |
| The boron concentration-related information of medical imaging data of the irradiated site is interpreted | |

| | S620 |
| --- | --- |
| A boron concentration of each voxel unit in the 3D voxel prosthesis tissue model is calculated according to the interpreted boron concentration-related information | |

| | S630 |
| --- | --- |
| The boron concentration data of each voxel unit is given according to a calculation result | |

FIG. 6

BORON NEUTRON CAPTURE THERAPY SYSTEM AND TREATMENT PLAN GENERATION METHOD THEREFOR

CROSS-REFERENCE TO RELATED PATENT APPLICATION

This application is a continuation application of International Application No. PCT/CN2021/119903, filed on Sep. 23, 2021, which claims priority to Chinese Patent Application No. 202011094034.3, filed on Oct. 14, 2020, the disclosures of which are hereby incorporated by reference.

TECHNICAL FIELD

An aspect of the invention relates to a radiotherapy system, and in particular to a boron neutron capture therapy (BNCT) system, and another aspect of the invention relates to a treatment plan generation method, and in particular to a method for generating a treatment plan of a BNCT system.

BACKGROUND

With the development of atomics, radioactive ray therapy, such as cobalt sixty, a linear accelerator, an electron beam, or the like, has become one of the major means to treat cancers. However, traditional photon or electron therapy is restricted by physical conditions of radioactive rays themselves, and thus will also harm a large number of normal tissues on a beam path while killing tumor cells. Furthermore, owing to different levels of sensitivity of tumor cells to radioactive rays, traditional radiotherapy usually has poor treatment effect on malignant tumors (for example, glioblastoma multiforme and melanoma) with radio resistance.

In order to reduce radiation injury to normal tissues around tumors, a target therapy concept in chemotherapy is applied to radioactive ray therapy. With respect to tumor cells with high radio resistance, irradiation sources with high relative biological effectiveness (RBE), such as proton therapy, heavy particle therapy, neutron capture therapy, or the like, are also developed actively now. Here neutron capture therapy combines the abovementioned two concepts, for example BNCT, provides a better cancer treatment choice than traditional radioactive rays, by specific aggregation of boron-containing drugs in tumor cells in combination with precise beam regulation and control.

A three-dimensional (3D) model is widely applied to the field of analysis and simulation of scientific experiments. For example, in the field of nuclear radiation and protection, in order to simulate absorption dose of a human body under a certain radiation condition to help a doctor to formulate a treatment plan, a computer technology is usually required to perform various processing on medical imaging data, so as to establish an accurate lattice model required by Monte Carlo software, and simulation and calculation are performed in combination with Monte Carlo software. In the field of neutron capture therapy, when a lattice model required by Monte Carlo software is established according to medical imaging data, and dose calculation and evaluation are performed, basic information of organisms reflected by each lattice, such as tissue types, boron concentration information, or the like, needs to be defined in the model, and accuracy and precision of the information determine reliability of a dose calculation result. Generally, the boron concentration information is to obtain boron concentration data of a sample according to blood sample test or slice test, so as to calculate corresponding tissue and tumor boron concentrations therefrom, so that a regional boron concentration value is given in a corresponding model region. Such given boron concentration information does not consider real distribution of boron drugs in the organism and metabolic condition of the boron drugs over time, thereby affecting reliability of the dose calculation result.

Therefore, it is necessary to provide a BNCT system and a method for generating a treatment plan thereof.

SUMMARY

In order to overcome defects of the related art, one aspect of the invention provides a BNCT system, including a neutron beam irradiation device, a treatment plan module and a control module. The neutron beam irradiation device generates a treatment neutron beam during irradiation treatment and irradiates the treatment neutron beam to an irradiated body who has ingested a boron ($^{10}$B)-containing drug, to form an irradiated site. The treatment plan module performs dose simulation and calculation and generates treatment plans according to medical imaging data of the irradiated site and parameters of the treatment neutron beam generated by the neutron beam irradiation device, the medical imaging data of the irradiated site includes tissue-related information and boron ($^{10}$B) concentration-related information. The control module retrieves a respective one of the treatment plans corresponding to the irradiated body from the treatment plan module, and controls the neutron beam irradiation device to perform irradiation treatment on the irradiated body according to the treatment plans. According to the boron concentration-related information of medical imaging data of the irradiated site, dose simulation and formulation of the treatment plan are performed, which may improve accuracy of model establishment and dose calculation.

Further, the treatment plan module may establish a corresponding 3D voxel prosthesis tissue model with tissue type data according to the tissue-related information, and give boron concentration data of each voxel unit in the 3D voxel prosthesis tissue model according to the boron concentration-related information. The boron concentration data is given according to the boron concentration-related information of medical imaging data of the irradiated site, which complies an actual situation better.

Preferably, the tissue-related information may be obtained by a non-radionuclide medical image of the irradiated site, and the treatment plan module automatically or manually defines a tissue type of each voxel unit in the 3D voxel prosthesis tissue model according to a conversion relationship between data of the non-radionuclide medical image and the tissue type. The 3D voxel prosthesis tissue model is established according to a conversion relationship between the medical imaging data and the tissue type, so that the tissue type (elementary composition) is provided more accurately, and the established geometric model is matched with an actual situation reflected by the medical imaging data better. Further, the non-radionuclide medical image is computed tomography (CT).

Preferably, the treatment plan module may give boron concentration data to different types of tissues of the 3D voxel prosthesis tissue model and is capable of giving different boron concentration data to tissues of the same type. According to an actual situation, boron concentration data is given, dose simulation and formulation of a treatment plan are performed, especially different boron concentration data are given to tissues of the same type, which may improve accuracy of model establishment and dose calculation.

Preferably, the boron concentration-related information may be obtained by a radionuclide medical image of the irradiated site, the irradiated body ingests a radiolabeled boron-containing drug or a non-boron-containing drug with a tumor cell affinity similar to that of the boron-containing drug to perform scanning of the radionuclide medical image, and the treatment plan module automatically or manually defines a boron concentration of each voxel unit in the 3D voxel prosthesis tissue model according to a conversion relationship between data of the radionuclide medical image and the boron concentration. Further, the radionuclide medical image may be positron emission tomography (PET), and the radiolabeled boron-containing drug may be $^{18}$F-BPA.

Preferably, the boron concentration-related information may include a body weight of the irradiated body, Body Weight, a drug injection dose, Injection Dose, a drug activity measure time, Measure Time, a radiography time, Scan Time, a radionuclide half time, Half Time, and an image lattice intensity, Image Pixel Intensity$_{pixel}$. The treatment plan module calculates a boron concentration of each voxel unit in the 3D voxel prosthesis tissue model according to the boron concentration-related information, and the treatment plan module gives the boron concentration data of each voxel unit in the 3D voxel prosthesis tissue model according to a calculation result. Further, the treatment plan module calculating the boron concentration of each voxel unit in the 3D voxel prosthesis tissue model according to the boron concentration-related information may include:

calculating an approximate blood image lattice intensity, Image Pixel Intensity$_{blood}$, by using formula 1:

$$(\text{formula 1})$$

$$SUV_{blood}[\text{g/ml}] =$$

$$\frac{\text{Image Pixel Intensity}_{blood}[\text{Bq/ml}] \times}{\text{Calibration Factor} \times \text{Body Weight}[\text{g}]}{\text{Injection Dose} [\text{Bq}] \times 2^{\frac{\text{Measure Time } [sec] - \text{Scan Time } [sec]}{\text{Half Time } [sec]}}} = 1$$

here $SUV_{blood}$ is a blood standard uptake value, and Calibration Factor is a correction value of a medical image scanning device; and calculating a ratio of the boron concentration of each voxel unit in the 3D voxel prosthesis tissue model to a blood boron concentration by using formula 2:

$$\frac{B_{pixel}[\text{ppm}]}{B_{blood}[\text{ppm}]} = \qquad (\text{formula 2})$$

$$\frac{SUV_{pixel}[\text{g/ml}]}{SUV_{blood}[\text{g/ml}]} = \frac{\text{Image Pixel Intensity}_{pixel}[\text{Bq/ml}]}{\text{Image Pixel Intensity}_{blood}[\text{Bq/ml}]}$$

here $B_{pixel}$ is a boron concentration of each voxel unit in the 3D voxel prosthesis tissue model, $B_{blood}$ is a blood boron concentration, and $SUV_p$ is a standard uptake value of each voxel unit in the 3D voxel prosthesis tissue model.

Further, the treatment plan module may simulate a boron dose $D_B$, a fast neutron dose $D_f$, an epithermal neutron dose $D_{epi}$, a thermal neutron dose $D_{th}$, and a photon dose $D_\gamma$ of the 3D voxel prosthesis tissue model per unit time by a Monte Carlo simulation program, and calculates an equivalent dose rate D of the 3D voxel prosthesis tissue model by using formula 3:

$$D(Gy-Eq)=CBE \times B_{pixel}(\text{ppm}) \times D_B(Gy/\text{ppm})+RBE_f \times D_f$$
$$(Gy)+RBE_{epi} \times D_{epi}(Gy)+RBE_{th} \times D_{th}(Gy)+RBE_\gamma \times$$
$$D_\gamma(Gy) \qquad (\text{formula 3})$$

here CBE is a compound biological effectiveness of a boron-containing drug per unit concentration, $RBE_f$ is a relative biological effectiveness of a fast neutron, and $RBE_{epi}$ is a relative biological effectiveness of an epithermal neutron, $RBE_{th}$ is a relative biological effectiveness of a thermal neutron, and $RBE_\gamma$ is a relative biological effectiveness of a photon.

Preferably, the treatment plan module may simulate a physical dose rate distribution of the irradiated site during irradiation treatment of the treatment neutron beam by a Monte Carlo simulation program, according to the parameters of the treatment neutron beam generated by the neutron beam irradiation device and the 3D voxel prosthesis tissue model with the tissue type data and the boron concentration data.

Further, the treatment plan module may perform an optimum selection to equivalent dose rate distributions simulated and calculated according to sampling of different irradiation angles, to select at least one irradiation angle.

Another aspect of the invention provides a method for generating a treatment plan of a BNCT system, including the following operations. A corresponding 3D voxel prosthesis tissue model with tissue type data is established according to tissue-related information of medical imaging data of an irradiated site. Boron ($^{10}$B) concentration data of each voxel unit in the 3D voxel prosthesis tissue model is given according to boron ($^{10}$B) concentration-related information of medical imaging data of the irradiated site. Beam parameters are defined in a Monte Carlo simulation program, and dose simulation and calculation is performed by sampling of different irradiation angles. An optimum selection is performed to the irradiation angles according to a calculation result, to generate the treatment plan. According to the boron concentration-related information of medical imaging data of the irradiated site, boron concentration data is given, and dose simulation and formulation of the treatment plan are performed, which complies with an actual situation better, and may improve accuracy of model establishment and dose calculation.

Preferably, the operation of giving boron concentration data of each voxel unit in the 3D voxel prosthesis tissue model according to boron concentration-related information of medical imaging data of the irradiated site may include the following operations. The boron concentration-related information of medical imaging data of the irradiated site is interpreted, to obtain a body weight of an irradiated body, Body Weight, a drug injection dose, Injection Dose, a drug activity measure time, Measure Time, a radiography time, Scan Time, a radionuclide half time, Half Time, and an image lattice intensity, Image Pixel Intensity$_{pixel}$. A boron concentration of each voxel unit in the 3D voxel prosthesis tissue model is calculated. The boron concentration data of each voxel unit in the 3D voxel prosthesis tissue model is given according to a calculation result. Further, the operation of calculating the boron concentration of each voxel unit in the 3D voxel prosthesis tissue model may include the following operations.

An approximate blood image lattice intensity, Image Pixel Intensity$_{blood}$, is calculated by using formula 1:

$$SUV_{blood}[\text{g/ml}] = \frac{\text{Image Pixel Intensity}_{blood}[\text{Bq/ml}] \times \text{Calibration Factor} \times \text{Body Weight[g]}}{\text{Injection Dose [Bq]} \times 2^{\frac{\text{Measure Time [sec]} - \text{Scan Time [sec]}}{\text{Half Time [sec]}}}} = 1 \quad \text{(formula 1)}$$

here $SUV_{blood}$ is a blood standard uptake value, and Calibration Factor is a correction value of a medical image scanning device.

A ratio of a boron concentration $B_{pixel}$ of each voxel unit in the 3D voxel prosthesis tissue model to a blood boron concentration $B_{blood}$ is calculated by using formula 2:

$$\frac{B_{pixel}[\text{ppm}]}{B_{blood}[\text{ppm}]} = \frac{SUV_{pixel}[\text{g/ml}]}{SUV_{blood}[\text{g/ml}]} = \frac{\text{Image Pixel Intensity}_{pixel}[\text{Bq/ml}]}{\text{Image Pixel Intensity}_{blood}[\text{Bq/ml}]} \quad \text{(formula 2)}$$

here $SUV_p$ is a standard uptake value of each voxel unit in the 3D voxel prosthesis tissue model.

Further, the operation of defining beam parameters in the Monte Carlo simulation program, and performing dose simulation and calculation by sampling of different irradiation angles may include the following operations. A physical dose received by each voxel unit of the 3D voxel prosthesis tissue model per unit time under a defined beam irradiation and at a sampled irradiation angle is simulated, the physical dose includes a boron dose $D_B$, a fast neutron dose $D_f$, an epithermal neutron dose $D_{epi}$, a thermal neutron dose $D_{th}$ and a photon dose $D_\gamma$. An equivalent dose rate D of each voxel unit of the 3D voxel prosthesis tissue model per unit time under a defined beam irradiation is calculated by using formula 3:

$$D(Gy-Eq) = CBE \times B_{pixel}(\text{ppm}) \times D_B(Gy/\text{ppm}) + RBE_f \times D_f(Gy) + RBE_{epi} \times D_{epi}(Gy) + RBE_{th} \times D_{th}(Gy) + RBE_\gamma \times D_\gamma(Gy) \quad \text{(formula 3)}$$

here CBE is a compound biological effectiveness of a boron-containing drug per unit concentration, $RBE_f$ is a relative biological effectiveness of a fast neutron, and $RBE_{epi}$ is a relative biological effectiveness of an epithermal neutron, $RBE_{th}$ is a relative biological effectiveness of a thermal neutron, and $RBE_\gamma$ is a relative biological effectiveness of a photon.

Yet another aspect of the invention provides a BNCT system, including a neutron beam irradiation device, a treatment plan module and a control module. The neutron beam irradiation device generates a treatment neutron beam during irradiation treatment and irradiates the treatment neutron beam to an irradiated body who has ingested a boron ($^{10}$B)-containing drug, to form an irradiated site. The treatment plan module defines tissue type and establish a 3D voxel prosthesis tissue model with tissue type data according to medical imaging data of the irradiated site. The treatment plan module gives boron concentration data to different types of tissues of the 3D voxel prosthesis tissue model and is capable of giving different boron concentration data to tissues of the same type. The treatment plan module performs dose simulation and calculation and generates treatment plans according to the 3D voxel prosthesis tissue model, the boron concentration data and parameters of the treatment neutron beam generated by the neutron beam irradiation device. The control module retrieves a respective one of the treatment plans corresponding to the irradiated body from the treatment plan module, and controls the neutron beam irradiation device to perform irradiation treatment on the irradiated body according to the respective one of the treatment plans. According to an actual situation, boron concentration data is given, dose simulation and formulation of a treatment plan are performed, especially different boron concentration data are given to tissues of the same type, which may improve accuracy of model establishment and dose calculation.

The BNCT system and the method for generating a treatment plan thereof provided in the invention may improve accuracy of model establishment and dose calculation.

BRIEF DESCRIPTION OF THE DRAWINGS

FIG. 1 is a schematic diagram of a boron neutron capture reaction.

FIG. 2 is an equation of a $^{10}$B(n,$\alpha$) $^7$Li neutron capture nuclear reaction.

FIG. 3 is a block diagram of a neutron capture therapy system according to an embodiment of the invention.

FIG. 4 is a flowchart of a method for generating a treatment plan by a treatment plan module according to an embodiment of the invention.

FIG. 5 is a flowchart of a method for establishing a 3D voxel prosthesis tissue model according to an embodiment of the invention.

FIG. 6 is a flowchart of a method for giving boron concentration data of each voxel unit in a 3D voxel prosthesis tissue model according to an embodiment of the invention

DETAILED DESCRIPTION

Figure 7:
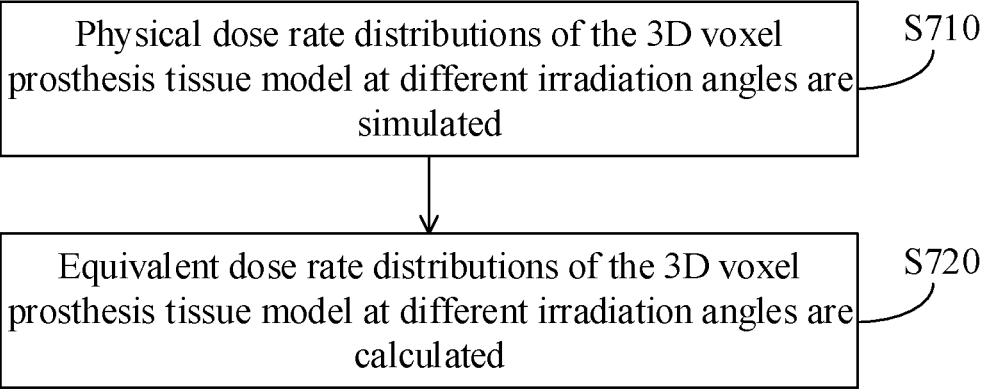
FIG. 7 is a flowchart of a method for dose simulation and calculation according to an embodiment of the invention.

Embodiments of the invention will be further described in detail below with reference to the drawings, to enable those skilled in the art to implement the embodiments with reference to texts of the description.

Preferably, a neutron capture therapy system and a method for generating a treatment plan thereof are taken as the embodiments of the invention. Neutron capture therapy, especially BNCT, will be briefly described below.

Application of neutron capture therapy as an effective means for cancer treatment gradually increases in recent years, in which BNCT is most commonly seen, and neutrons supplied to BNCT may be supplied by a nuclear reactor or accelerator. The embodiments of the invention take an accelerator BNCT as an example, and basic components of the accelerator BNCT generally include an accelerator for accelerating charged particles (such as protons, deuterium cores, or the like), a target, a thermal removal system and a beam shaping body, here the accelerated charged particles act with the metal target to generate neutrons, and an appropriate nuclear reaction may be selected according to characteristics such as a desired neutron yield and energy, available energies of the accelerated charged particles, a current, physical and chemical properties of the metal target, or the like. Nuclear reactions as commonly discussed include $^7$Li(p, n) $^7$Be and $^9$Be(p, n) $^9$B, both of which are endothermic reactions and have energy thresholds of 1.881 MeV and 2.055 MeV respectively. An ideal neutron source for BNCT is an epithermal neutron at a keV energy level, then theoretically, when protons with energies only slightly higher than the threshold are used to bombard a metallic lithium target, neutrons with relatively low energies may be generated for clinical application without too much retarding treatment. However, action sections of lithium (Li) and beryllium (Be) metallic targets with protons of threshold energies are not high, therefore protons with higher energies are usually selected to initiate a nuclear reaction, to generate a large enough neutron flux.

BNCT produces two heavily charged particles $^4$He and $^7$Li by using a characteristic of a boron ($^{10}$B)-containing drug having a high capture section for a thermal neutron, and through $^{10}$B (n, α) $^7$Li neutron capture and a nuclear fission reaction. Referring to FIGS. 1 and 2, a schematic diagram of a boron neutron capture reaction, and an equation of a $^{10}$B (n, α) $^7$Li neutron capture nuclear reaction are shown respectively, and the two charged particles have an average energy of about 2.33 MeV, and have characteristics of high linear energy transfer (LET) and short range. LET and range of a particle are 150 keV/μm and 8 μm respectively, LET and range of the heavily charged particle $^7$Li are 175 keV/μm and 5 μm respectively, and the two particles have a total range approximately equivalent to a cell size, so that radiation injury to an organism may be limited to a cell level. When boron-containing drugs are selectively aggregated in tumor cells, a purpose of locally killing tumor cells may be achieved with an appropriate neutron radioactive source, on premise of not inducing too large injury to normal tissues.

A Monte Carlo method may accurately simulate collision trajectories and energy distributions of nuclear particles in a 3D space within an irradiation target. In neutron capture therapy, in order to simulate absorption dose of a human body under a certain radiation condition to help a doctor to formulate a treatment plan, a computer technology is usually required to perform various processing on medical imaging data, so as to establish an accurate lattice model required by Monte Carlo software, and simulation and calculation are performed in combination with Monte Carlo software. The medical imaging data may be magnetic resonance imaging (MRI), computed tomography (CT), positron emission tomography (PET), PET-CT or X-ray imaging. However, it is well known by those skilled in the art that other medical imaging data may also be used as long as other medical imaging data may be converted into a 3D voxel prosthesis tissue model, to be applied to the radiotherapy system and the method for generating a treatment plan thereof disclosed in the invention.

Referring to FIG. 3, the radiotherapy system according to the embodiment is preferably a BNCT system 100, including a neutron beam irradiation device 10, a treatment plan module 20 and a control module 30. The neutron beam irradiation device 10 includes a neutron generation device 11 and a treatment table 12, and the neutron generation device 12 generates a treatment neutron beam N during irradiation treatment and irradiates the treatment neutron beam to a patient who has ingested a boron ($^{10}$B)-containing drug on the treatment table 12, to form an irradiated site. Before treatment, the treatment plan module 20 generates treatment plans according to medical imaging data of the irradiated site of the patient and parameters of the treatment neutron beam N generated by the neutron generation device 11. During irradiation treatment, the control module 30 retrieves a respective one of the treatment plans corresponding to a current patient from the treatment plan module 20, and controls irradiation of the neutron beam irradiation device 10 according to the treatment plan.

In an embodiment, a patient is required to ingest a radiolabeled boron ($^{10}$B)-containing drug before treatment, and boron ($^{10}$B) concentration-related information is obtained by a radionuclide medical image (such as PET). That is, the medical imaging data of the irradiated site of the patient includes tissue-related information and boron concentration-related information, here the tissue-related information may be obtained from the radionuclide medical image simultaneously, or may be obtained from other non-radionuclide medical images (such as CT). It may be understood that the radionuclide medical image may also be PET-CT, or the like, and the non-radionuclide medical image may also be MRI, or the like, which is not specifically limited in the invention. The treatment plan module 20 establishes a corresponding 3D voxel prosthesis tissue model with tissue type data and tissue density data according to the tissue-related information of medical imaging data of the irradiated site, gives boron concentration data of each voxel unit in the 3D voxel prosthesis tissue model according to the boron concentration-related information of medical imaging data of the irradiated site, simulates and calculates a dose distribution of the patient during irradiation treatment by a Monte Carlo simulation program, according to the parameters of the treatment neutron beam N generated by the neutron generation device 11 and the 3D voxel prosthesis tissue model with the tissue type data, the tissue density data and the boron concentration data, and generates a treatment plan. It may be understood that tissue density may not be defined either. According to the boron concentration-related information of medical imaging data of the irradiated site, boron concentration data is given, and dose simulation and formulation of the treatment plan are performed, which complies with an actual situation better, and may improve accuracy of model establishment and dose calculation.

Referring to FIG. 4, a method for generating a treatment plan by a treatment plan module 20 according to an embodiment specifically includes the following operations S410 to S440.

In operation S410, a corresponding 3D voxel prosthesis tissue model with tissue type data and tissue density data is established according to tissue-related information of medical imaging data of an irradiated site.

In operation S420, boron concentration data of each voxel unit in the 3D voxel prosthesis tissue model is given according to boron concentration-related information of medical imaging data of the irradiated site.

In operation S430, beam parameters are defined in a Monte Carlo simulation program (such as Monte Carlo N Particle (MCNP) Transport Code), and dose simulation and calculation is performed by sampling of different irradiation angles.

In operation S440, an optimum selection is performed to the irradiation angles according to a calculation result, to generate the treatment plan.

Referring to FIG. 5, in an embodiment, the operation S410 of establishing the 3D voxel prosthesis tissue model according to the medical imaging data may further include the following operations S510 to S550.

In operation S510, medical imaging data is read.

In operation S520, a 3D medical imaging voxel model is established.

In operation S530, boundaries of a region of interest (ROI) are defined or read.

In operation S540, tissue type (elementary composition) and tissue density of each voxel unit are defined. The tissue type and tissue density of each voxel unit may be automatically defined according to a conversion relationship between CT imaging data and the tissue type and tissue density, or may be manually defined by a user, for example, a specific tissue type and tissue density may be given to each voxel unit within boundaries of a ROI.

In operation S550, the 3D voxel prosthesis tissue model is established.

The 3D voxel prosthesis tissue model is established according to a conversion relationship between the medical imaging data and the tissue type and tissue density, so that the tissue type (elementary composition) and tissue density are provided more accurately, and the established geometric model is matched with an actual situation reflected by the medical imaging data better. A detailed process of establishing the 3D voxel prosthesis tissue model according to the medical imaging data may refer to a patent application published on Mar. 8, 2017 with a publication number CN 106474634 A, and entitled "METHOD FOR ESTABLISHING GEOMETRIC MODEL BASED ON MEDICAL IMAGING DATA", which is incorporated here by reference in its entirety.

According to operation S420, boron concentration data of each voxel unit in the 3D voxel prosthesis tissue model is given according to the boron concentration-related information of medical imaging data of the irradiated site, and based on a geometric model marked with tissue boron concentration information, concentration of a boron-containing drug in each tissue may be clearly known, and then an actual situation is more truly reflected during neutron irradiation simulation. The boron concentration-related information is obtained by a radionuclide medical image of the irradiated site, the irradiated body ingests a radiolabeled boron-containing drug to perform scanning of the radionuclide medical image, and the treatment plan module automatically or manually defines a boron concentration of each voxel unit in the 3D voxel prosthesis tissue model according to a conversion relationship between data of the radionuclide medical image and the boron concentration. In an embodiment, the radionuclide medical image is PET, and the radiolabeled boron-containing drug ingested by the irradiated body is $^{18}$F-BPA. It may be understood that $^{18}$F-BPA may also be replaced by other radioactive labels or other boron-containing drugs, or may be a radiolabeled non-boron-containing drug with a tumor cell affinity similar to that of the boron-containing drug, such as $^{18}$F-FDG. Since BPA or the like which may be used as boron-containing drugs for BNCT generally have high price at present, boron-containing drugs are replaced by non-boron-containing drugs to perform simulation of the treatment plan, which may reduce cost greatly.

Referring to FIG. 6, in an embodiment, the operation S420 may further include the following operations S610 to S630.

In operation S610, the boron concentration-related information of medical imaging data of the irradiated site, that is, boron concentration-related medical imaging data information, Information Object Definition (IOD), obtained by scanning of the radionuclide medical image, is interpreted.

The medical imaging data usually uses a Digital Imaging and Communications In Medicine (DICOM) format, and the boron concentration-related IOD in DICOM data includes a body weight of the irradiated body (Body Weight), a drug injection dose (Injection Dose), a drug activity measure time (Measure Time), a radiography time (Scan Time), a radionuclide half time (Half Time), and it may be understood that the boron concentration-related IOD may further include a drug type (Radiopharmaceutical) or the like. Such information may be determined when scanning of the radionuclide medical image is started, information source may be manually input by an operator, or may be automatically obtained or retrieved, as shown in Table 1, in which a data tag (Tag) of the boron concentration-related information in DICOM data and a corresponding data name (Description) are listed:

TABLE 1

| boron concentration-related IOD in DICOM data IOD | |
| --- | --- |
| Tag | Description |
| (0018, 0031) | Radiopharmaceutical |
| (0018, 1072) | Measure Time |
| (0018, 1074) | Injection Dose |
| (0018, 1075) | Half Time |
| (0008, 0031) | Scan Time |
| (0010, 1030) | Body Weight |

The boron concentration-related IOD in DICOM data further includes an image lattice intensity (Image Pixel Intensity), scanning of the radionuclide medical image (such as PET) uses a positive and negative electron pair annihilation reaction occurred by positron generated by decay of the radionuclide meeting electrons in the tissue, and at this time, a detector such as a photomultiplier tube (PMT) or the like may be used to detect γ rays emitted therefrom, and then a computer forms a cross-section image reflecting distribution of positron radioactive isotopes. In an embodiment, $^{18}$F-BPA-PET scanning is used, original data of each lattice of the image is a counting rate of photons generated by mutual destruction of positron released by $^{18}$F decay and electrons, which is converted into an image lattice intensity (Image Pixel Intensity$_{pixel}$) of each lattice of PET image as the output of medical imaging data, and $^{18}$F is marked in BPA, therefore original data on the PET image may be used as a basis for quantification of $^{10}$B. It may be understood that when a radiolabeled non-boron-containing drug with a tumor cell affinity similar to that of the boron-containing drug is used to perform scanning of the radionuclide medical image, original data on the image may also be used as a basis for quantification of $^{10}$B.

In operation S620, a boron concentration of each voxel unit in the 3D voxel prosthesis tissue model is calculated according to the interpreted boron concentration-related information.

Standard uptake value (SUV) is a semi-quantitative indicator collected by the radionuclide medical image, and refers to a ratio of a radioactivity of a developer (radiolabeled drug) taken by a local tissue to an average injection activity of the whole body. As shown in formula 1, SUV of a corresponding lattice may be obtained by the boron concentration-related IOD in operation S610, and each lattice scanned by the radionuclide medical image corresponds to each voxel unit in the 3D voxel prosthesis tissue model one-to-one.

$$SUV[\text{g/ml}] = \qquad\qquad\qquad\qquad\text{(formula 1)}$$

$$\frac{\text{Average radioactivity per unit volume } [\text{Bq/ml}]}{\text{Injected radioactivity } [\text{Bq}]/\text{Body Weight[g]}} =$$

$$\frac{\text{Image Pixel Intensity[Bq/ml]} \times \text{Calibration Factor} \times \text{Body Weight [g]}}{\text{Injection Dose [Bq]} \times 2^{\frac{Measure\ Time\ [sec]\ -Scan\ Time\ [sec]}{Half\ Time\ [sec]}}}$$

A SUV value of blood is set to 1, that is, a radioactivity of blood is approximately considered to be equal to an average injection radioactivity of the whole body. Original data of the radionuclide medical image when $SUV_{blood}=1$, that is, an approximate blood image lattice intensity (Image Pixel Intensity$_{blood}$), is obtained by formula 2.

$$SUV_{blood}[\text{g/ml}] =$$
$$\frac{\text{Image Pixel Intensity}_{blood}[\text{Bq/ml}] \times \text{Calibration Factor} \times \text{Body Weight}[\text{g}]}{\text{Injection Dose }[\text{Bq}] \times 2^{\frac{\text{Measure Time }[sec] - \text{Scan Time }[sec]}{\text{Half Time }[sec]}}} = 1$$

(formula 2)

here $SUV_{blood}$ is a blood standard uptake value, and Calibration Factor is a correction value of a medical image scanning device.

Furthermore, a ratio of each lattice to blood boron concentration is obtained by a ratio of each lattice to the blood standard uptake value, that is, a ratio of the boron concentration of each voxel unit in the 3D voxel prosthesis tissue model to a blood boron concentration is calculated by using formula 3.

$$\frac{B_{pixel}[\text{ppm}]}{B_{blood}[\text{ppm}]} =$$
$$\frac{SUV_{pixel}[\text{g/ml}]}{SUV_{blood}[\text{g/ml}]} = \frac{\text{Image Pixel Intensity}_{pixel}[\text{Bq/ml}]}{\text{Image Pixel Intensity}_{blood}[\text{Bq/ml}]}$$

(formula 3)

here $B_{pixel}$ is a boron concentration of each voxel unit in the 3D voxel prosthesis tissue model, $B_{blood}$ is a blood boron concentration, and $SUV_{pixel}$ is a standard uptake value of each voxel unit in the 3D voxel prosthesis tissue model.

The boron concentration of each voxel unit in the 3D voxel prosthesis tissue model is converted to $SUV_{pixel}/SUV_{blood}$ by using the blood boron concentration as a reference value, that is, the ratio of the boron concentration of each voxel unit to the blood boron concentration may be obtained, and a non-uniform boron concentration distribution is established. After a blood boron concentration value is obtained by drawing blood for detection, or the like, a specific boron concentration value of each voxel unit may be obtained.

In operation S630, the boron concentration data of each voxel unit is given according to a calculation result. The boron concentration data may be automatically given according to the calculation result, or may be manually given by the user, for example, a specific boron concentration data is given to each voxel unit within boundaries of a ROI according to the calculation result.

By calculation, an actual situation is complied better, the treatment plan module gives boron concentration data to different types of tissues of the 3D voxel prosthesis tissue model and is capable of giving different boron concentration data to tissues of the same type, which may improve accuracy of model establishment and dose calculation. After establishing the 3D voxel prosthesis tissue model with tissue type and tissue boron concentration, collision trajectories and energy distributions of nuclear particles in an interior 3D space when the patient is irradiated by neutron beams in BCNT may be simulated by a Monte Carlo simulation program, that is, a physical dose rate distribution may be simulated, an equivalent dose rate distribution is calculated according to the physical dose rate distribution, and then a treatment plan solution is screened according to dose indexes. Specifically, referring to FIG. 7, operation S430 includes the following operations S710 and S720.

In operation S710, beam parameters (such as beam energy, intensity, radius, or the like) are defined in a Monte Carlo simulation program, and physical dose rate distributions of the 3D voxel prosthesis tissue model at different irradiation angles are simulated by sampling of different irradiation angles, that is, a physical dose received by each voxel unit of the 3D voxel prosthesis tissue model per unit time under a defined beam irradiation and at a sampled irradiation angle is simulated.

During sampling, a starting position and a beam angle of beam calculation are required to be determined, and the starting position and angle during calculation may be determined by a forward algorithm or a reverse algorithm. In the forward algorithm, the starting position is determined as an in-vitro position, and sampling and calculation may be sequentially performed according to a fixed angle or distance interval, or may also be performed in a random sampling manner; the beam angle may be set as a direction of vector from an irradiation point to a centroid or deepest part of the tumor, and a specific endpoint position of the tumor may be adjusted according to user requirements. In the reverse algorithm, the starting position is determined in a range of the tumor, may be a centroid or deepest part of the tumor, or a random point in the range of the tumor, and the beam angle may be set by randomly sampling or sampling according to a specified interval.

During sampling, beam angles may also be screened, for example, beam angle evaluation is performed, and a beam angle for subsequent calculation is selected according to an evaluation result. Or, beam angles are screened after sampling and calculation, for example, screening is performed according to a result of radiation dose distribution or a result of beam angle evaluation. A method for evaluating beam angles is not described in detail here, and may refer to a patent application published on Jun. 16, 2017 with a publication number CN 106853272 A, and entitled "METHOD FOR EVALUATING BEAM IRRADIATION ANGLES", which is incorporated here by reference in its entirety.

Major factors for dose contribution in BNCT have three parts:

1) Boron dose $D_B$: coming from $\alpha$, $^7$Li particles with high LET resulting from a $^{10}$B (n, $\alpha$) $^7$Li neutron capture reaction of a boron-containing drug in a tissue and tumor with neutrons.

2) Neutron dose: divided into a fast neutron dose $D_f$, an epithermal neutron dose $D_{epi}$ and a thermal neutron dose $D_{th}$ according to neutron energies, here for composition elements of a tissue organ, dose is mainly a dose caused by rebound protons generated by an elastic scattering effect of a $^1$H (n, n')p neutron and hydrogen, a dose resulting from protons generated by a $^{14}$N (n, p) $^{14}$C action and rebound carbon ions, and a micro-dose of neutrons and other elements.

3) Photon dose $D_\gamma$: containing action of neutrons with a shielding structure, and a capture reaction with human tissues to induce photons, and the latter mainly generates 2.22 MeV photons by a $^1$H (n, $\gamma$) $^2$H reaction of thermal neutrons.

In an embodiment, in operation S710, the physical dose received per unit time includes a boron dose $D_B$, a fast neutron dose $D_f$, an epithermal neutron dose $D_{epi}$, a thermal neutron dose $D_{th}$ and a photon dose $D_\gamma$ per unit time obtained by simulation through the Monte Carlo simulation program.

In operation S720, equivalent dose rate distributions of the 3D voxel prosthesis tissue model at different irradiation angles are calculated.

In BNCT, due to different biological effectiveness caused by photons and neutrons, RBE of different tissues are multiplied for dose items of fast neutron, epithermal neutron, thermal neutron and photon respectively, to obtain an equivalent dose. In terms of boron dose, due to each of $\alpha$, $^7$Li particles having a short range, injury is usually limited to an occurrence position of boron neutron capture action, and different types of cells have different capabilities of absorbing boron-containing drugs, so that boron concentration is not uniformly distributed in vivo. In order to obtain an equivalent dose, the dose item must be multiplied by CBE of each tissue and a corresponding boron concentration (defined in operation S630), that is, an equivalent dose rate D of a voxel unit is calculated by using formula 4:

$$D(Gy\text{-}Eq)=\text{CBE}\times B_{pixel}(\text{ppm})\times D_B(Gy/\text{ppm})+\text{RBE}_f\times D_f$$
$$(Gy)+\text{RBE}_{epi}\times D_{epi}(Gy)+\text{RBE}_{th}\times D_{th}(Gy)+\text{RBE}_\gamma\times$$
$$D_\gamma(Gy) \qquad \text{(formula 4)},$$

here CBE is a compound biological effectiveness of a boron-containing drug per unit concentration, $\text{RBE}_f$ is RBE of a fast neutron, $\text{RBE}_{epi}$ is RBE of an epithermal neutron, $\text{RBE}_{th}$ is RBE of a thermal neutron, and $\text{RBE}_\gamma$ is RBE of a photon.

In operation S440, according to the equivalent dose rate distribution calculated in operation S720, different treatment plan solutions (irradiation angles and corresponding irradiation time) are evaluated or optimized in combination with a mathematical algorithm. For example, a ROI region is selected as a target, irradiation time corresponding to a sampled irradiation angle is obtained by taking a maximum dose, an average dose, a prescription dose or the like of the ROI region as constraint conditions, an equivalent dose distribution of the 3D voxel prosthesis tissue model at the sampled irradiation angle is obtained at the irradiation time, and then equivalent dose distributions obtained by simulating and calculating in the 3D voxel prosthesis tissue model at different irradiation angles and corresponding irradiation time are evaluated or optimized by using a dose volume histogram (DVH), an isodose curve, a dose table or the like. The irradiation angle evaluation as described above may also be performed to evaluate, so that an operator such as a doctor or another person selects a treatment plan solution which meets requirements better. It may be understood that at least two irradiation angles may also be selected through an optimization algorithm or the like to sequentially irradiate the patient, a specific number of irradiation angles may be manually set, or may be automatically obtained through an algorithm, or arc-shaped continuous regulation and control of irradiation angles may be used, and sampling of the irradiation angle may be performed on the same side or opposite side of the patient.

It may be understood that some simple transformations of the formula 1 to formula 4 and dose calculation, evaluation and optimum selection methods still fall within the scope of protection of the invention.

It may be understood that the invention may also be applied to diseases which may be treated with BNCT, such as Alzheimer's disease and rheumatoid arthritis, and tumor cells are other lesion tissues, and the patient may also be another irradiated body.

While the illustrative specific implementations of the invention have been described as above, so that those skilled in the art understand the invention, it should be apparent that the invention is not limited to the scope of the specific implementations, various changes are apparent for those of ordinary skill in the art and fall within the scope of protection of the invention, as long as these changes fall within the spirit and scope of the invention as defined and determined by the appended claims.

What is claimed is:

1. A boron neutron capture therapy (BNCT) system, characterized in that the BNCT system comprises:
   a neutron beam irradiation device generating a treatment neutron beam during irradiation treatment and irradiating the treatment neutron beam to an irradiated body who has ingested a boron-containing drug, to form an irradiated site;
   a treatment plan module performing dose simulation and calculation and generating treatment plans according to medical imaging data of the irradiated site and parameters of the treatment neutron beam generated by the neutron beam irradiation device, the medical imaging data of the irradiated site comprising tissue-related information and boron concentration-related information; and
   a control module retrieving a respective one of the treatment plans corresponding to the irradiated body from the treatment plan module, and controlling the neutron beam irradiation device to perform irradiation treatment on the irradiated body according to the treatment plans.

2. The BNCT system of claim 1, wherein the treatment plan module establishes a corresponding three-dimensional (3D) voxel prosthesis tissue model with tissue type data according to the tissue-related information, and gives boron concentration data of each voxel unit in the 3D voxel prosthesis tissue model according to the boron concentration-related information.

3. The BNCT system of claim 2, wherein the tissue-related information is obtained by a non-radionuclide medical image of the irradiated site, and the treatment plan module automatically or manually defines a tissue type of each voxel unit in the 3D voxel prosthesis tissue model according to a conversion relationship between data of the non-radionuclide medical image and the tissue type.

4. The BNCT system of claim 2, wherein the treatment plan module gives boron concentration data to different types of tissues of the 3D voxel prosthesis tissue model and is capable of giving different boron concentration data to tissues of the same type.

5. The BNCT system of claim 2, wherein the boron concentration-related information is obtained by a radionuclide medical image of the irradiated site, the irradiated body ingests a radiolabeled boron-containing drug or a non-boron-containing drug with a tumor cell affinity similar to that of the boron-containing drug to perform scanning of the radionuclide medical image, and the treatment plan module automatically or manually defines a boron concentration of each voxel unit in the 3D voxel prosthesis tissue model according to a conversion relationship between data of the radionuclide medical image and the boron concentration.

6. The BNCT system of claim 5, wherein the radionuclide medical image is positron emission tomography (PET), and the radiolabeled boron-containing drug is 18F-BPA.

7. The BNCT system of claim 2, wherein the boron concentration-related information comprises a body weight of the irradiated body, Body Weight, a drug injection dose, Injection Dose, a drug activity measure time, Measure Time, a radiography time, Scan Time, a radionuclide half time, Half Time, and an image lattice intensity, Image Pixel Intensity$_{pixel}$.

8. The BNCT system of claim 7, wherein the treatment plan module calculates a boron concentration of each voxel unit in the 3D voxel prosthesis tissue model according to the boron concentration-related information;

the treatment plan module gives the boron concentration data of each voxel unit in the 3D voxel prosthesis tissue model according to a calculation result.

9. The BNCT system of claim 8, wherein the treatment plan module calculating the boron concentration of each voxel unit in the 3D voxel prosthesis tissue model according to the boron concentration-related information comprises:

calculating an approximate blood image lattice intensity, Image pixel Intensity$_{blood}$, by using formula 1:

$$SUV_{blood}[\text{g/ml}] = \qquad \text{(formula 1)}$$

$$\dfrac{\text{Image Pixel Intensity}_{blood}[\text{Bq/ml}] \times \text{Calibration Factor} \times \text{Body Weight [g]}}{\text{Injection Dose [Bq]} \times 2^{\frac{Measure\ Time\ [sec] - Scan\ Time\ [sec]}{Half\ Time\ [sec]}}} = 1$$

wherein SUV$_{blood}$ is a blood standard uptake value, and Calibration Factor is a correction value of a medical image scanning device; and calculating a ratio of the boron concentration of each voxel unit in the 3D voxel prosthesis tissue model to a blood boron concentration by using formula 2:

$$\dfrac{B_{pixel}[\text{ppm}]}{B_{blood}[\text{ppm}]} = \qquad \text{(formula 2)}$$

$$\dfrac{SUV_{pixel}[\text{g/ml}]}{SUV_{blood}[\text{g/ml}]} = \dfrac{\text{Image Pixel Intensity}_{pixel}[\text{Bq/ml}]}{\text{Image Pixel Intensity}_{blood}[\text{Bq/ml}]}$$

wherein B$_{pixel}$ is a boron concentration of each voxel unit in the 3D voxel prosthesis tissue model, B$_{blood}$ is a blood boron concentration, and SUV$_{pixel}$ is a standard uptake value of each voxel unit in the 3D voxel prosthesis tissue model.

10. The BNCT system of claim 9, wherein the treatment plan module simulates a boron dose DB, a fast neutron dose D$_f$, an epithermal neutron dose D$_{epi}$, a thermal neutron dose D$_{th}$ and a photon dose Dy of the 3D voxel prosthesis tissue model per unit time by a Monte Carlo simulation program, and calculates an equivalent dose rate D of the 3D voxel prosthesis tissue model by using formula 3:

$$D(Gy-Eq) = CBE \times B_{pixel}(\text{ppm}) \times D_B(Gy/\text{ppm}) + RBE_f \times D_f(Gy) + RBE_{epi} \times D_{epi}(Gy) + RBE_{th} \times D_{th}(Gy) + RBE_\gamma \times D_\gamma(Gy) \qquad \text{(formula 3)}$$

wherein CBE is a compound biological effectiveness of a boron-containing drug per unit concentration, RBE$_f$ is a relative biological effectiveness of a fast neutron, and RBE$_{epi}$ is a relative biological effectiveness of an epi-thermal neutron, RBE$_{th}$ is a relative biological effec-tiveness of a thermal neutron, and RBE$_\gamma$ is a relative biological effectiveness of a photon.

11. The BNCT system of claim 2, wherein the treatment plan module simulates a physical dose rate distribution of the irradiated site during irradiation treatment of the treat-ment neutron beam by a Monte Carlo simulation program, according to the parameters of the treatment neutron beam generated by the neutron beam irradiation device and the 3D voxel prosthesis tissue model with the tissue type data and the boron concentration data.

12. The BNCT system of claim 11, wherein the treatment plan module performs an optimum selection to equivalent dose rate distributions simulated and calculated according to sampling of different irradiation angles, to select at least one irradiation angle.

13. A method for generating a treatment plan of a boron neutron capture therapy (BNCT) system, characterized in that the method comprises:

establishing a corresponding three-dimensional (3D) voxel prosthesis tissue model with tissue type data according to tissue-related information of medical imaging data of an irradiated site;

giving boron concentration data of each voxel unit in the 3D voxel prosthesis tissue model according to boron concentration-related information of medical imaging data of the irradiated site;

defining beam parameters in a Monte Carlo simulation program, and performing dose simulation and calcula-tion by sampling of different irradiation angles; and performing an optimum selection to the irradiation angles according to a calculation result, to generate the treat-ment plan.

14. The method for generating a treatment plan of claim 13, wherein the step of establishing a corresponding three-dimensional (3D) voxel prosthesis tissue model with tissue type data according to tissue-related information of medical imaging data of an irradiated site comprises:

reading medical imaging data;

establishing a 3D medical imaging voxel model;

defining or reading boundaries of a region of interest;

defining tissue type of each voxel unit;

establishing a 3D voxel prosthesis tissue model.

15. The method for generating a treatment plan of claim 13, wherein the step of giving boron concentration data of each voxel unit in the 3D voxel prosthesis tissue model according to boron concentration-related information of medical imaging data of the irradiated site comprises:

interpreting the boron concentration-related information of medical imaging data of the irradiated site;

calculating a boron concentration of each voxel unit in the 3D voxel prosthesis tissue model; and giving the boron concentration data of each voxel unit in the 3D voxel prosthesis tissue model according to a calculation result.

16. The method for generating a treatment plan of claim 15, wherein the medical image is a radionuclide medical image.

17. The method for generating a treatment plan of claim 15, the boron concentration-related information comprises a body weight of the irradiated body, Body Weight, a drug injection dose, Injection Dose, a drug activity measure time, Measure Time, a radiography time, Scan Time, a radionu-clide half time, Half Time, and an image lattice intensity, Image Pixel Intensity$_{pixel}$.

18. The method for generating a treatment plan of claim 17, wherein the step of calculating the boron concentration of each voxel unit in the 3D voxel prosthesis tissue model comprises:

calculating an approximate blood image lattice intensity, Image Pixel Intensity$_{blood}$ by using formula 1:

$$SUV_{blood}[\text{g/ml}] =$$

$$\frac{\text{Image Pixel Intensity}_{blood}[\text{Bq/ml}] \times \text{Calibration Factor} \times \text{Body Weight [g]}}{\text{Injection Dose [Bq]} \times 2^{\frac{Measure\ Time\ [sec] - Scan\ Time\ [sec]}{Half\ Time\ [sec]}}} = 1$$

(formula 1)

wherein $SUV_{blood}$ is a blood standard uptake value, and Calibration Factor is a correction value of a medical image scanning device; and calculating a ratio of a boron concentration $B_{pixel}$ of each voxel unit in the 3D voxel prosthesis tissue model to a blood boron concentration $B_{blood}$ by using formula 2:

$$\frac{B_{pixel}[\text{ppm}]}{B_{blood}[\text{ppm}]} =$$

(formula 2)

$$\frac{SUV_{pixel}[\text{g/ml}]}{SUV_{blood}[\text{g/ml}]} = \frac{\text{Image Pixel Intensity}_{pixel}[\text{Bq/ml}]}{\text{Image Pixel Intensity}_{blood}[\text{Bq/ml}]}$$

wherein $SUV_{pixel}$ is a standard uptake value of each voxel unit in the 3D voxel prosthesis tissue model.

19. The method for generating a treatment plan of claim 18, wherein the step of defining beam parameters in the Monte Carlo simulation program, and performing dose simulation and calculation by sampling of different irradiation angles comprises:

simulating a physical dose received by each voxel unit of the 3D voxel prosthesis tissue model per unit time under a defined beam irradiation and at a sampled irradiation angle, the physical dose comprising a boron dose $D_B$, a fast neutron dose $D_f$, an epithermal neutron dose $D_{epi}$, a thermal neutron dose $D_{th}$ and a photon dose $D_\gamma$; and calculating an equivalent dose rate D of each voxel unit of the 3D voxel prosthesis tissue model per unit time under a defined beam irradiation by using formula 3:

$$D(Gy-Eq) = CBE \times B_{pixel}(\text{ppm}) \times D_B(Gy/\text{ppm}) + RBE_f \times D_f(Gy) + RBE_{epi} \times D_{epi}(Gy) + RBE_{th} \times D_{th}(Gy) + RBE_\gamma \times D_\gamma(Gy)$$

(formula 3)

wherein CBE is a compound biological effectiveness of a boron-containing drug per unit concentration, $RBE_f$ is a relative biological effectiveness of a fast neutron, and $RBE_{epi}$ is a relative biological effectiveness of an epithermal neutron, $RBE_{th}$ is a relative biological effectiveness of a thermal neutron, and RBE is a relative biological effectiveness of a photon.

20. A boron neutron capture therapy (BNCT) system, characterized in that the BNCT system comprises:

a neutron beam irradiation device generating a treatment neutron beam during irradiation treatment and irradiates the treatment neutron beam to an irradiated body who has ingested a boron (1°B)-containing drug, to form an irradiated site;

a treatment plan module defining tissue type and establish a 3D voxel prosthesis tissue model with tissue type data according to medical imaging data of the irradiated site, and giving boron concentration data to different types of tissues of the 3D voxel prosthesis tissue model, and giving different boron concentration data to tissues of the same type; and the treatment plan module performing dose simulation and calculation and generating treatment plans according to the 3D voxel prosthesis tissue model, the boron concentration data and parameters of the treatment neutron beam generated by the neutron beam irradiation device; and a control module retrieving a respective one of the treatment plans corresponding to the irradiated body from the treatment plan module, and controlling the neutron beam irradiation device to perform irradiation treatment on the irradiated body according to the respective one of the treatment plans.

*     *     *     *     *